(12) United States Patent
Doerr

(10) Patent No.: US 8,280,507 B2
(45) Date of Patent: Oct. 2, 2012

(54) CARDIAC STIMULATOR FOR TREATMENT OF TACHYCARDIAC ARRHYTHMIAS OF THE HEART

(75) Inventor: Thomas Doerr, Berlin (DE)

(73) Assignee: BIOTRONIK CRM Patent AG (CH)

( * ) Notice: Subject to any disclaimer, the term of this patent is extended or adjusted under 35 U.S.C. 154(b) by 618 days.

(21) Appl. No.: 12/481,687

(22) Filed: Jun. 10, 2009

(65) Prior Publication Data

US 2009/0312812 A1 Dec. 17, 2009

(30) Foreign Application Priority Data

Jun. 11, 2008 (DE) .................. 10 2008 002 370

(51) Int. Cl.
*A61N 1/05* (2006.01)
(52) U.S. Cl. .......................................... 607/5
(58) Field of Classification Search .............. 607/4–8
See application file for complete search history.

(56) References Cited

U.S. PATENT DOCUMENTS

| | | | |
|---|---|---|---|
| 5,193,550 A | 3/1993 | Duffin | |
| 5,558,098 A | 9/1996 | Fain | |
| 5,776,168 A | 7/1998 | Gunderson | |
| 7,149,569 B1 | 12/2006 | Fain | |
| 7,167,747 B2 | 1/2007 | Gunderson et al. | |
| 7,248,925 B2 | 7/2007 | Bruhns et al. | |
| 7,274,961 B1 | 9/2007 | Kroll et al. | |
| 2005/0149135 A1 | 7/2005 | Krig et al. | |
| 2005/0177194 A1 | 8/2005 | Bjorling | |
| 2007/0038253 A1 | 2/2007 | Kim et al. | |
| 2008/0065161 A1 | 3/2008 | Lian et al. | |

FOREIGN PATENT DOCUMENTS

| | | |
|---|---|---|
| EP | 1 774 988 A | 4/2007 |
| EP | 18 97 587 A2 | 3/2008 |
| WO | WO 97/36647 A | 10/1997 |
| WO | WO 03/105952 A1 | 12/2003 |
| WO | WO 2004/103172 A | 12/2004 |

OTHER PUBLICATIONS

European Patent Office, Search Report for corresponding EP09160086.6 (Jul. 8, 2009).

*Primary Examiner* — Scott Getzow
*Assistant Examiner* — Amanda Patton
(74) *Attorney, Agent, or Firm* — Craig A. Fieschko, Esq.; DeWitt Ross & Stevens S.C.

(57) ABSTRACT

An implantable antitachycardiac cardiac stimulator has at least one right-ventricular sensing unit, a defibrillation shock generator and a control unit, as well as an additional detection unit for detecting ventricular events which operates independently of the right-ventricular detection electrode, and an evaluation unit (e.g., as an additional component of the control unit) which suppresses the delivery of a defibrillation shock on reliable detection of the normal rhythm via the additional detection unit.

20 Claims, 8 Drawing Sheets

CARDIAC STIMULATOR FOR TREATMENT OF TACHYCARDIAC ARRHYTHMIAS OF THE HEART

FIELD OF THE INVENTION

The invention relates to an implantable cardiac stimulator designed as a cardioverter/defibrillator (ICD) for delivering a defibrillation shock in the event of ventricular fibrillation. The cardiac stimulator may also be designed as a single-chamber cardiac stimulator, a biventricular cardiac stimulator, or the like.

BACKGROUND OF THE INVENTION

Implantable cardiac stimulators in the form of cardiac pacemakers or cardioverter/defibrillators are known in the prior art. Such cardiac stimulators are usually connected to electrode lines, which have stimulation electrodes and optionally additional defibrillation electrodes in the immediate vicinity. A cardiac pacemaker can deliver an electric stimulation pulse to the muscle tissue of a cardiac chamber via a stimulation electrode to thereby induce a stimulated contraction of the cardiac chamber, provided the stimulation pulse is of sufficient intensity and the myocardial tissue (myocardium) is not at that moment in a refractory phase. Electrode lines having relatively small-area stimulation electrodes are generally used for this purpose, since it is usually sufficient if only a small portion of the myocardium of the cardiac chamber is initially stimulated when triggering stimulated contraction. Within the context of this discussion, such stimulated contraction of the cardiac chamber will be referred to as a "stimulated" event, whereas if there is a natural contraction of the cardiac chamber, this is regarded as an "intrinsic" or "natural" cardiac activity. For example, contraction of the right atrium of the heart can be referred to as an atrial event, which may be a natural atrial event, or in the case of an atrial pacemaker, it may also be a stimulated atrial event. Natural (intrinsic) and stimulated left-ventricular and right-ventricular events can be distinguished in the same manner.

Local stimulation of the myocardium propagates from the stimulus site by stimulus conduction in the myocardium, and leads to depolarization of the muscle cells and thus to contraction of the myocardium. After a short period of time, there is repolarization of the muscle cells and thus relaxation of the myocardium. During the depolarization phase, the myocardial cells are not responsive to stimulation, i.e., they are refractory. The electric potentials associated with depolarization and repolarization can be detected, and their characteristics recorded over time—known as an electrocardiogram—can be evaluated.

Such natural (intrinsic) events are detected by deriving the electric potentials of the myocardium of the respective cardiac chamber with the help of sensing electrodes, which are part of a corresponding electrode line. The sensing electrodes may at the same time be the stimulation electrodes, and may also be used as stimulation electrodes and as sensing electrodes in alternation. A pair of sensing electrodes including two neighboring electrodes, namely a tip electrode and a ring electrode, where the tip electrode also serves as a stimulation electrode, is typically used for sensing, i.e., detection of intrinsic events. Bipolar derivation of an intracardiac electrocardiogram (IEGM) can be achieved in this manner. Sensing and stimulation in the ventricle are performed with the help of a ventricular electrode line, and stimulation and sensing in the atrium (right atrium) are performed with an atrial electrode line, each connected separately to a respective cardiac stimulator. In addition, a left-ventricular electrode line may also be provided, typically protruding through the coronary sinus and a lateral vein branching off from the former into the vicinity of the left ventricle, where it may have a small-area stimulation electrode and/or sensing electrode.

The sensing electrodes are connected to corresponding sensing units during operation of the cardiac stimulator, these units being designed to evaluate a respective electrocardiogram recorded via a sensing electrode (and/or a sensing electrode pair) and in particular to detect intrinsic atrial and/or ventricular events, i.e., natural atrial or ventricular contractions. This is accomplished, e.g., by threshold value comparison, i.e., an intrinsic event is detected when the respective intracardiac electrocardiogram exceeds a suitably predefined threshold value.

The respective intrinsic atrial heart rate (atrial frequency) and/or ventricular heart rate (ventricular frequency) can be derived from the frequency at which atrial and ventricular events follow one another, and tachycardias can be detected, for example.

In addition to the properties of the pacemaker already described above, an implantable cardioverter/defibrillator may also deliver a stronger current pulse to the heart, such that this pulse should not only stimulate (depolarize) a small portion of the myocardium but should also depolarize the largest possible amount of the myocardium and thereby make it refractory, to thereby interrupt a cycling stimulation of the myocardium, which is typical of fibrillations. Such a pulse is known as a defibrillation shock. It is typically delivered via a large-area defibrillation electrode in comparison with the stimulation electrode or sensing electrode.

Such a defibrillation electrode is often implemented in the form of a shock coil on the exterior surface of the electrode line in the respective cardiac chamber. For example, a ventricular electrode line may have a ventricular shock coil, in addition to a tip electrode or a ring electrode for stimulation and sensing, and may also have a proximal shock coil that is situated in the superior vena cava after implantation.

As a rule, a defibrillation shock is delivered when the cardiac stimulator detects a fibrillation, i.e., an irregular high-frequency intrinsic cardiac activity, which is also known as ventricular fibrillation, an event resulting in incomplete contraction of the respective cardiac chamber. Such a fibrillation is classified as a tachycardiac arrhythmia, which includes tachycardias (e.g., ventricular flutter) in addition to fibrillations. In contrast with fibrillation, tachycardia is regularly followed by a complete contraction of the cardiac chamber affected, but at a higher rate than would be physiologically appropriate. Such tachycardias can often be treated by anti-tachycardiac stimulation and do not require a defibrillation shock. Fibrillations are usually treated with a defibrillation shock.

For detection of ventricular fibrillation, a detection unit is typically provided as a component of a control unit of a cardiac stimulator; and is connected to the right-ventricular sensing unit and is designed to perform primary ventricular fibrillation detection on the basis of the right-ventricular intracardiac electrocardiogram (IEGM) derived using bipolar leads. If a predefined detection condition (X-of-Y criterion) is met, the detection unit indicates a ventricular fibrillation.

In tachycardiac arrhythmias of the ventricle, a distinction is made between supraventricular tachycardias (SVT) and ventricular tachycardias (VT) in the narrower sense. The latter have their origin in the ventricle itself, whereas supraventricular tachycardias have their origin in the atrium. For the treatment initiated after detection of a tachycardia, the type of ventricular tachycardia (ventricular tachycardia in the narrower sense (VT) or supraventricular tachycardia (SVT)) is significant.

Treatment of tachycardias and fibrillations by means of intracardiac electrotherapy can be performed in various known ways. It is known to apply antitachycardiac stimulation (antitachycardia pacing, ATP) in the form of overdrive stimulation in which stimulation pulses are delivered at a stimulation rate, which is increased in comparison with the prevailing intrinsic (tachycardiac) heart rate, or in the form of delivery of cardioversion shocks or delivery of defibrillation shocks, whereby the former usually have a lower energy than the latter. Defibrillation shocks should make the entire myocardium of the affected cardiac chamber refractory at the same time, and therefore temporarily unresponsive to stimulation to thereby interrupt a cycling stimulation of the respective myocardium.

Treatment of ventricular tachycardias (VT) in the narrower sense by overdrive stimulation within the context of antitachycardiac pacing (ATP) should have the result that a reentry cycle of stimulation of the myocardium, which is typical of ventricular tachycardias (VT), is interrupted by a stimulation pulse which occurs before the natural (intrinsic) stimulation of the affected cardiac chamber. This requires reliable detection of intrinsic ventricular contractions prior to triggering of the ATP.

The present invention is based on the problem that oversensing of ventricular events may occur under some circumstances, i.e., the corresponding ventricular sensing unit detects more presumably ventricular events than actually occur. In many cases, such oversensing results in delivery of inadequate defibrillation shocks or at least results in the start of charging operations due to a perceived interference signal in the right-ventricular electrode. The service lifetime of an ICD is significantly reduced by such charging operations.

SUMMARY OF THE INVENTION

An object of the present invention is to prevent, whenever possible, inadequate delivery of defibrillation shocks or unnecessary initiation of charging operations due to oversensing. This object may be achieved by an implantable antitachycardiac cardiac stimulator having at least:
- a right-ventricular sensing unit for detecting right-ventricular events by means of at least one detecting electrode (sensing electrode) in the right ventricle to which the right-ventricular sensing is (or can be) connected via a right-ventricular electrode line,
- a defibrillation shock generator, which can generate a defibrillation shock as a function of the detection unit and deliver it via at least one defibrillation shock electrode,
- a control unit designed as a detection unit for detecting ventricular fibrillation (VF) on the basis of detected right-ventricular events and to trigger the defibrillation shock generator, as well as
- an additional detection unit for detection of ventricular events, operating independently of the right-ventricular detection electrode electrode and
- an evaluation unit (e.g., as another component of the control unit), which suppresses the delivery of a defibrillation shock when a normal rhythm is definitively detected with the additional detection unit.

With a biventricular cardiac stimulator having a terminal for a left-ventricular electrode line, e.g., a coronary sinus (CS) electrode line, the additional detection unit is preferably connected to the left-ventricular electrode line and/or its terminal. The evaluation unit is then designed to detect a normal rhythm on the basis of an ECG signal to be obtained by a left-ventricular sensing electrode. To do so, the evaluation unit may be connected to a left-ventricular sensing unit and may be designed for analysis of left-ventricular sensing events detected by the left-ventricular sensing unit.

A triple-chamber cardiac stimulator having terminals for a left-ventricular electrode line and a right-ventricular electrode line is especially preferred.

In conjunction with the latter version of the additional detection unit, the evaluation unit is preferably designed to evaluate a rhythm as being a "normal rhythm" if, after an atrial event (A sense, A pace) within a time slot, preferably programmable (expected AV time), a single left-ventricular event is detected, and also the interval of the left-ventricular events corresponds to the previous atrial events plus a tolerance.

The expected AV time here for left-ventricular detection after atrial events is preferably adjustable by the physician.

Additionally or alternatively, the additional detection unit may also be designed for deriving a far-field electrocardiogram, e.g., between a shock electrode and an electrically conductive housing of an ICD.

To this end, the implantable cardiac stimulator preferably has a housing which has a surface that is at least partially electrically conductive, and has a defibrillation electrode line terminal for connection of a ventricular defibrillation electrode line, such that the defibrillation electrode line terminal has an electric contact which is connected to an opposite contact, which is connected to the defibrillation electrode in the case of a defibrillation electrode line connected to the cardiac stimulator. The additional detection unit according to this version has a far-field electrocardiogram detection unit, which has a first input that is preferably connected to a terminal for a ventricular defibrillation electrode and a second input which is preferably connected to the electrically conductive surface of the housing of the cardiac stimulator. The far-field electrocardiogram detection unit is designed to generate a far-field electrocardiogram on the basis of the electric potentials applied at both inputs during operation.

In this version, the additional detection unit also has a far-field electrocardiogram evaluation unit, which is connected to the far-field electrocardiogram detection unit and is designed to detect signal features, e.g., QRS complexes, that are characteristic of ventricular depolarization in a far-field electrocardiogram generated by the far-field electrocardiogram detection unit. Ventricular depolarizations characterize intrinsic ventricular actions, i.e., intrinsic (natural) ventricular events. Such an implantable cardiac stimulator may detect right-ventricular events independently of the right-ventricular sensing electrode, and makes it possible to perform a plausibility test on the ventricular events detected by the right-ventricular sensing electrode.

In combination with the latter version of the additional detection unit, the evaluation unit is preferably designed to evaluate a rhythm as being a normal rhythm when QRS complexes can definitely be detected in the far-field electrocardiogram.

The additional detection unit and/or its far-field electrocardiogram evaluation unit are preferably designed to detect a QRS complex in the far-field electrocardiogram by pattern comparison.

Alternatively, the additional detection unit and/or its far-field electrocardiogram evaluation unit may be designed to detect sensing events in the far-field electrocardiogram by comparison with a fixedly predefined or variable threshold value.

According to another version of the cardiac stimulator, it may have a defibrillation electrode line terminal which is suitable for connection of a ventricular defibrillation electrode line having two shock coils, namely a proximal shock coil (e.g., provided for arrangement in the superior vena cava) and a distal shock coil. The cardiac stimulator may be designed so that the two shock coils are to be connected to the far-field electrocardiogram detection unit of the additional detection unit independently of one another. This is preferably designed to be connected to the proximal shock coil of the two available shock coils in order to determine the far-field electrocardiogram from the potential difference between the proximal shock coil and the electrically conductive surface of the cardiac stimulator housing.

In an alternative version, the cardiac stimulator may also be designed so that the far-field electrocardiogram detection unit of the additional detection unit is optionally to be connected to a proximal shock coil or a distal shock coil of a ventricular defibrillation electrode line.

Other variations of the connection of the additional detection unit to different electrodes for the purposes of recording a far-field electrocardiogram include:
- the additional detection unit is connected to a distal shock electrode and to the housing of the ICD for derivation of the far-field electrocardiogram in order to derive the far-field electrocardiogram between these electrodes;
- the additional detection unit is connected to a proximal shock electrode and to the housing of the ICD for derivation of the far-field electrocardiogram in order to derive the far-field electrocardiogram between these electrodes;
- the additional detection unit is connected to a distal shock electrode and a proximal shock electrode of the ICD for derivation of the far-field electrocardiogram in order to derive the far-field electrocardiogram between these electrodes;
- the additional detection unit is connected to an atrial sensing or stimulation electrode and to the housing of the ICD for derivation of the far-field electrocardiogram in order to derive the far-field electrocardiogram between these electrodes.

The cardiac stimulator is preferably designed to store the information about a suppressed defibrillation shock in the implant, so it can be read out and displayed by a programming device.

The cardiac stimulator is further preferably designed to store the information about a suppressed defibrillation shock and automatically transmit it to a telemonitoring system via a wireless data transmission interface.

In other preferred version of the invention, the cardiac stimulator has a stimulation mode for clinical examinations, in which the cardiac stimulator supplies only diagnostic information in the sense described previously by actually suppressing any shocks.

Furthermore, the cardiac stimulator preferably has a VT/SVT evaluation unit designed to perform a classification of a ventricular tachyarrhythmia as a supraventricular tachycardia (SVT) or as a ventricular tachycardia (VT) on the basis of successive detected atrial events and successive ventricular events.

Additional advantageous versions of the cardiac stimulator can be derived from combinations of the foregoing features, though such versions are not mentioned explicitly here.

BRIEF DESCRIPTION OF THE DRAWINGS

The invention will now be explained in greater detail on the basis of an exemplary version of the invention with reference to the figures, in which.

DETAILED DESCRIPTION OF PREFERRED VERSIONS OF THE INVENTION

Figure 1:
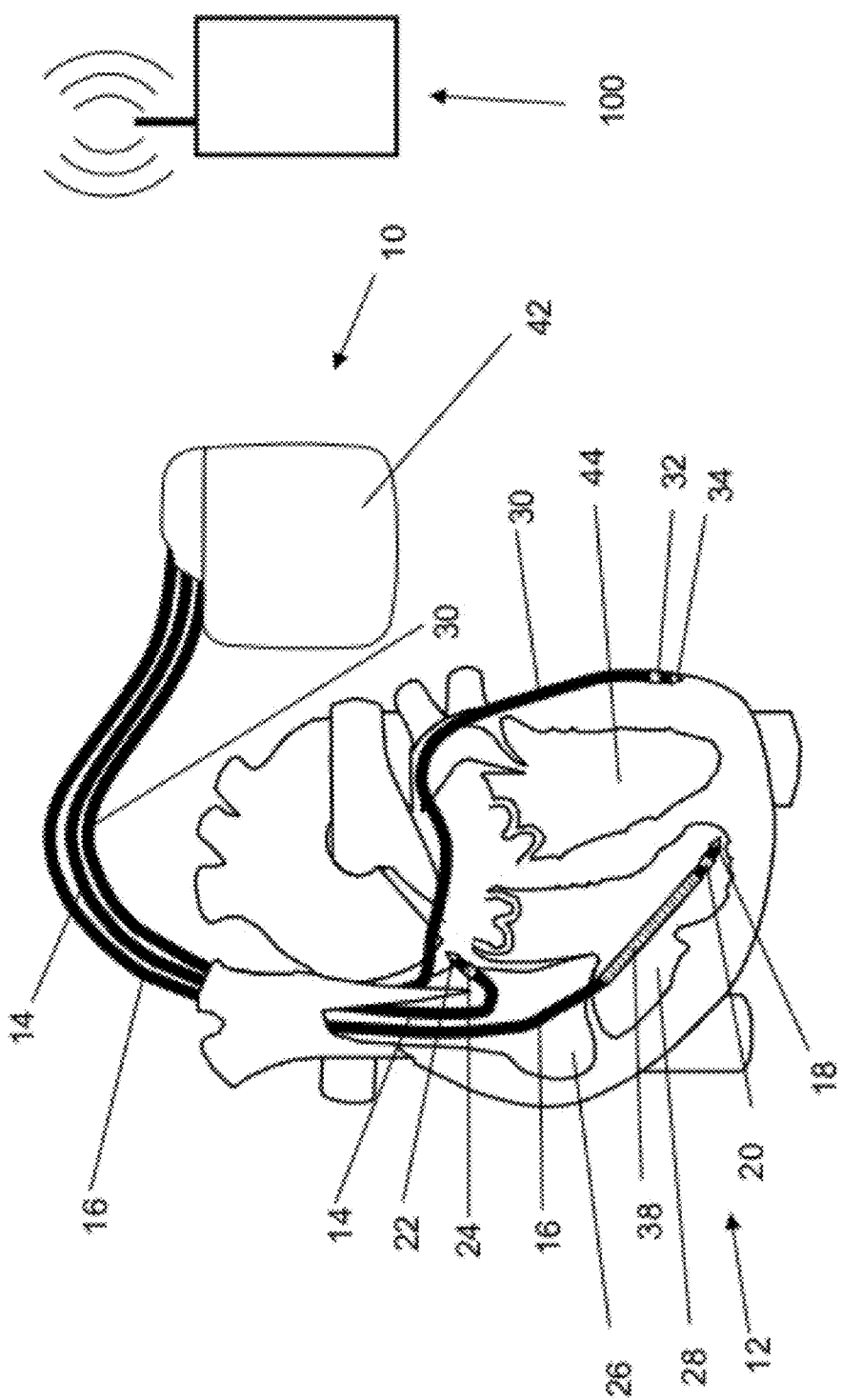
FIG. 1: shows a cardiac stimulator in the form of an implantable triple-chamber cardioverter/defibrillator (ICD) system in combination with electrode lines connected to it.

FIG. 1 shows an implant 10 in the form of a biventricular triple-chamber cardiac pacemaker and cardioverter/defibrillator (ICD). Three electrode lines are connected to it, namely a right-atrial electrode line 14, a right-ventricular electrode line 16 and a left-ventricular electrode line 30. In the implanted state, the right-atrial electrode line 14 ends in the right atrium 26 of the heart 12. The right-ventricular electrode line 16 ends in the right ventricle 28 of the heart 12, and the left-ventricular electrode line 30 extends through the coronary sinus of the heart 12 up to the left ventricle 44 of the heart.

On its distal end, the right-atrial electrode line 14 has a right-atrial tip electrode (RA tip) 22 and, at a slight distance from that, a right-atrial ring electrode (RA ring) 24. Similarly, the right-ventricular electrode line 16 has on its distal end the right-ventricular tip electrode (RV tip) 18 and, at a slight distance from that, a right-ventricular ring electrode (RV ring) 20. A left-ventricular tip electrode (LV tip) 34 is attached to the distal end of the left-ventricular electrode line 30 and, at a slight distance from that, a left-ventricular ring electrode (LV ring) 32 is also attached. These electrodes serve to pick up electric potentials in the respective cardiac chamber and to deliver stimulation pulses to the respective cardiac chamber in normal pacemaker operation. The right-ventricular electrode line 16 also has a right-ventricular shock coil (defibrillation electrode) 38 situated in the right ventricle in the implanted state.

Figure 2:
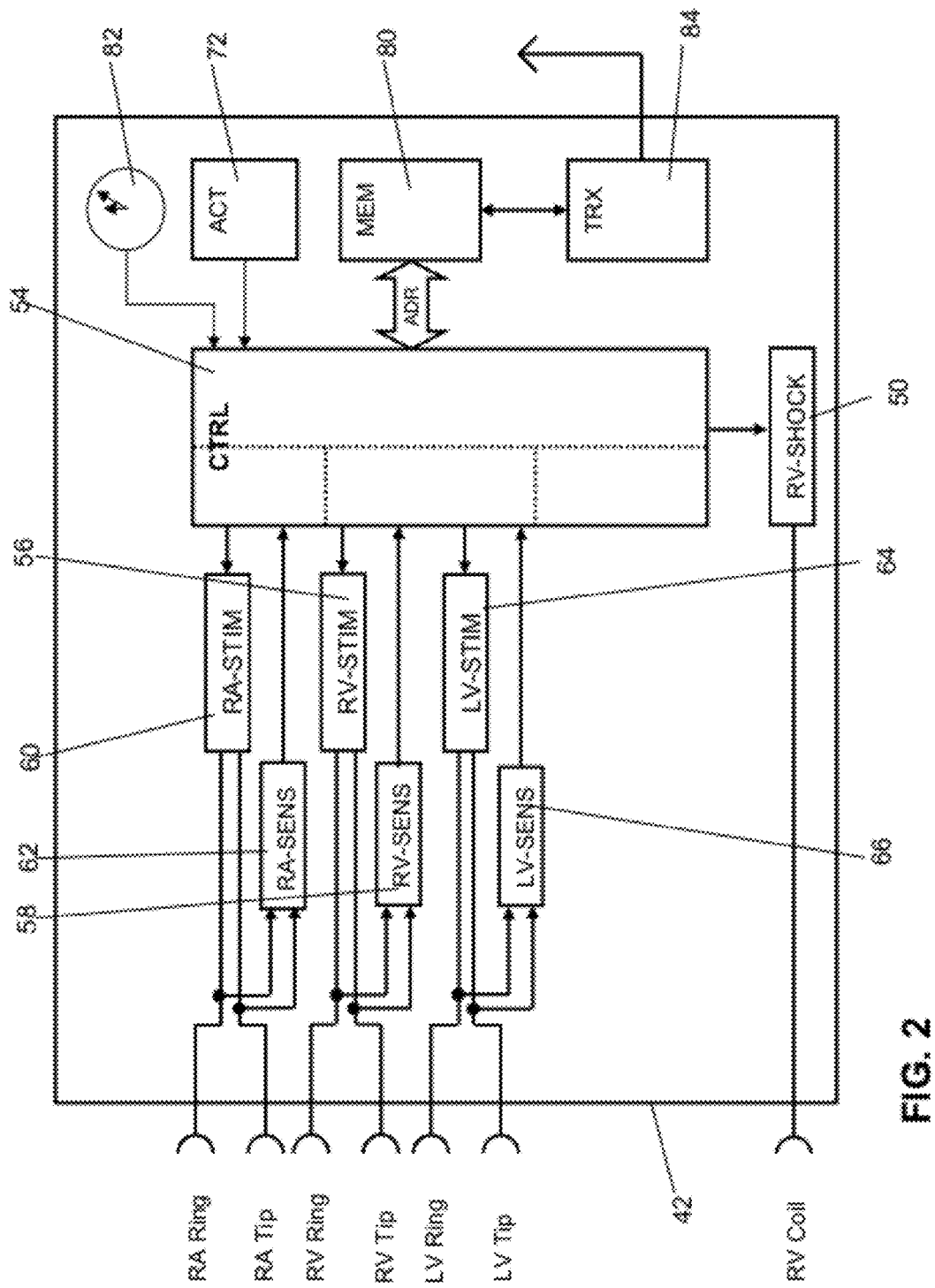
FIG. 2: shows a schematic block diagram of the cardiac stimulator from FIG. 1.

FIG. 2 shows the main components of the cardiac stimulator 10. The electric terminals for the various electrodes 18, 20, 24, 22, 32 34 and 38 are shown on the left side. The shock electrode 38 is connected to a right-ventricular shock pulse generator 50. The shock generator 50 is connected to a stimulation control unit 54, which triggers the shock pulse generator 50 to generate and deliver a defibrillation shock as needed.

The terminal for the right-ventricular tip electrode (RV tip) 18 and the terminal for the right-ventricular ring electrode (RV ring) 20 are each connected to a right-ventricular stimulation unit 56 as well as to a right-ventricular sensing unit 58.

The right-ventricular stimulation unit 56 as well as the right-ventricular sensing unit 58 are each connected to the stimulation control unit 54.

The right-ventricular stimulation unit 56 is designed to generate a right-ventricular stimulation pulse in response to a control signal from the stimulation control unit 54 and then to deliver this pulse to the right-ventricular ring electrode (RV ring) 20 and the right-ventricular tip electrode (RV tip) 18. Alternatively, it is also possible for the housing 42 of the cardiac stimulator 10 to form a neutral electrode, and for the right-ventricular stimulation unit 56 to be connected to the terminal for the right-ventricular tip electrode (RV tip) 18 and the housing 42 as another electrode for delivering a stimulation pulse. A right-ventricular stimulation pulse differs from a defibrillation shock in that the stimulation pulse has a much lower pulse intensity, such that it does not stimulate all the cardiac tissue (myocardium) of a cardiac chamber all at once, as does a defibrillation shock, but instead it stimulates only the myocardial cells in the immediate vicinity of the right-ventricular tip electrode RV tip 18. The stimulus then propagates through natural stimulus conduction over the entire right ventricle 28 and thereby ensures a stimulated contraction of the right ventricle 28.

The right-ventricular sensing unit 58 is designed to first amplify and filter the electric potentials applied to the terminal for the right-ventricular ring electrode (RV ring) 20 and the right-ventricular tip electrode (RV tip) 18 through an input amplifier. In addition, the right-ventricular sensing unit 58 is designed to evaluate the course of the electric signals applied at its inputs, such that the right-ventricular sensing unit 58 automatically detects a natural (intrinsic), i.e., automatic, contraction of the right ventricle 28. This may be accomplished, for example, by comparing the characteristic of the signal applied to the inputs of the right-ventricular sensing 58 with a threshold value. The greatest amplitude of the signal in the form of the so-called R wave is typically characteristic of the natural contraction of the right ventricle 28, which can be detected by threshold value comparison. The right-ventricular sensing unit 58 then delivers a corresponding output signal indicating a natural contraction of the right ventricle 28 to the stimulation control unit 54.

Similarly, the terminal for the right-atrial tip electrode (RA tip) 22 and the terminal for the right-atrial ring electrode (RA ring) 24 are each connected to both a right-atrial stimulation unit 60 and a right-atrial sensing unit 62, each in turn being connected to the stimulation control unit 54. The right-atrial stimulation unit 60 is designed to generate stimulation pulses of a sufficient intensity to stimulate the right-atrial myocardium. The right-atrial stimulation pulses may have a different pulse intensity than the right-ventricular stimulation pulses. The right-atrial sensing unit 62 is designed to detect a so-called P wave from the characteristic of the differential signal applied at its inputs, wherein the P wave characterizes a natural (intrinsic) contraction of the right atrium 26. If the right-atrial sensing unit 62 detects a corresponding P wave, it generates an output signal and forwards it to the stimulation control unit 54, which characterizes a natural contraction of the right atrium 26.

In the same way, the terminal for the left-ventricular tip electrode LV tip 34 and the terminal for the left-ventricular electrode LV ring 32 are also connected to a left-ventricular stimulation unit 64 and a left-ventricular sensing unit 66. The left-ventricular stimulation unit 64 and the left-ventricular sensing unit 66 are likewise connected to the stimulation control unit 54. Both of them function like the stimulation units 56 and 60 and sensing units 58 and 62 described above.

As another component of the cardiac stimulator 10, an activity sensor 72 is connected to the stimulation control unit 54 and is integrated into the housing 42 of the cardiac stimulator 10. The activity sensor 72 is designed to detect a motion signal depending on the patient's physical activity and to output a corresponding signal indicating the patient's physical activity to the stimulation control unit 54. This allows the stimulation control unit 54 to adapt the timing of the stimulation pulses to patient's needs (hemodynamic demand).

In addition, the cardiac stimulator 10 includes a memory unit 80, which is connected to the stimulation control unit 54 and allows signals generated or evaluated by the stimulation control unit 54 to be stored. The memory unit 80 also allows control programs for the stimulation control unit 54 to be stored in a variable form. Furthermore, the stimulation control unit 54 is connected to a timer 82.

The memory unit 80 is connected to a telemetry unit 84 which allows the data stored in the memory unit 80 to be transferred to an external device (not shown), or programming commands from the external device may be transferred to the cardiac stimulator 10 and stored in the memory unit 80.

The control unit 54 is designed to perform a primary ventricular fibrillation detection (VF detection) on the basis of right-ventricular IEGMs recorded by the right-ventricular sensing unit on the basis of bipolar leads. To do so, the control unit 54 has an interval classification unit 220 (see FIG. 3). If a predefined detection condition (X-of-Y criterion) is met, the control unit 54 checks by means of an additional detection unit and an evaluation unit 280 (see FIG. 3) to determine whether the sequences of events recorded via the atrial electrode 14 and the left-ventricular electrode 30 meet a defined time condition which is inconsistent with ventricular fibrillation. In this case, the delivery of a defibrillation shock is suppressed; otherwise, the shock is delivered as normal. The occurrence of a left-ventricular event (sense) in a defined time slot after atrial stimulation or detection is checked and the atrial interval length is compared with the left-ventricular interval length.

Figure 3:
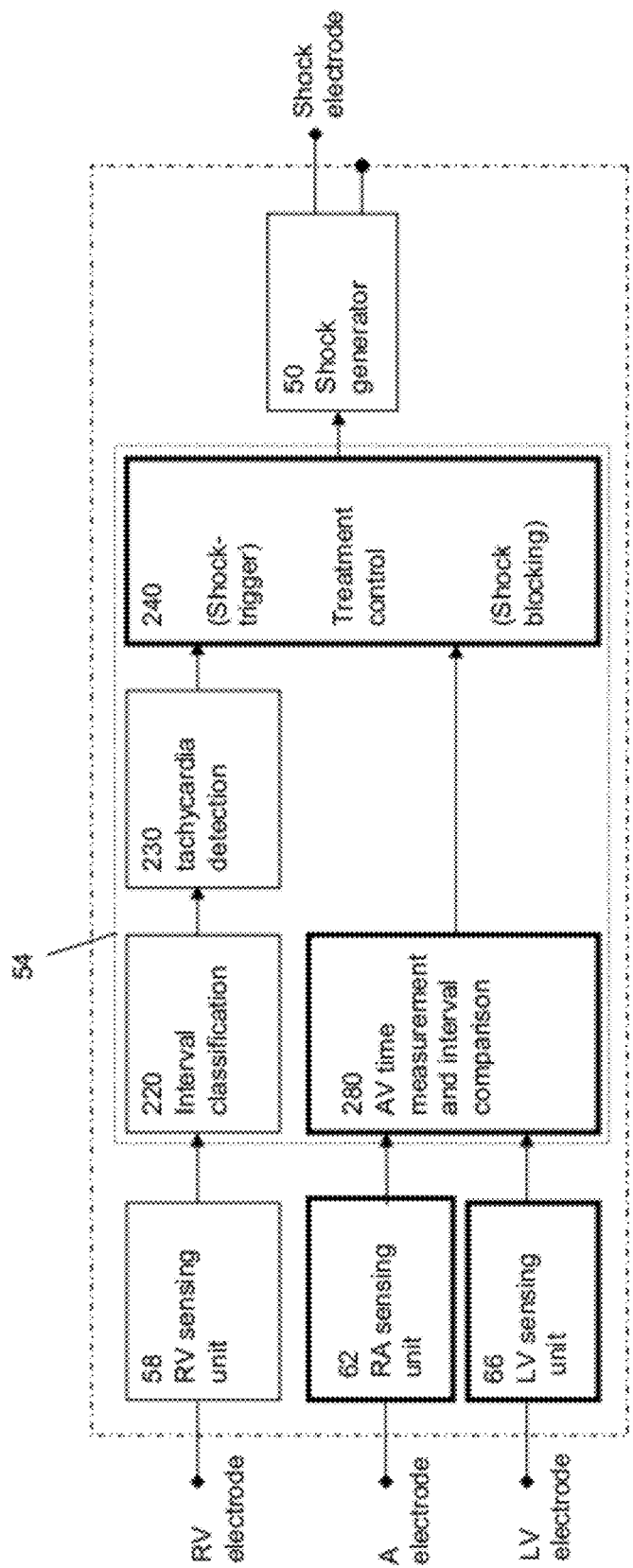
FIG. 3: shows a block diagram of a few relevant components of a triple-chamber ICD system.

FIG. 3 shows a few of the relevant components of the cardiac stimulator 10, in particular the control unit 54. As described, the cardiac stimulator 10 has terminals for a right-ventricular (RV) electrode line 16, an atrial (A) electrode line 14 and a left-ventricular (LV) electrode line 30, with corresponding stimulation and detection electrodes. Defibrillation shocks may be delivered via the defibrillation shock electrode 38 and the housing 42 as the counterelectrode for delivery of the shock.

The right-ventricular electrode line 16 is connected to the right-ventricular sensing unit 58. This sensing unit 58 amplifies, digitizes and filters the IEGM derived by the sensing electrodes 18 and 20, extracting from it the points in time of the right-ventricular depolarization (sense). These sense events are then evaluated according to the interval length by an interval classifier 220 as a component of the control unit 54 and then sent to a detection counter 230 as an additional component of the control unit 54 for ventricular fibrillation (VF) detection. This VF detection counter 230 is preferably an X-of-Y counter, i.e., the VF zone limit must be exceeded in order to meet the VF detection criterion X-of-Y intervals that have elapsed. If this VF criterion is met, then a trigger signal is sent to the treatment control unit 240 as a component of the control unit 54 for initiation of shock therapy with the programmed parameters. This treatment control unit 240 then triggers the charging of the high-voltage capacitors and the subsequent delivery of a shock by the shock generator 50.

The atrial electrode line 14 and the left-ventricular electrode line 30 are each also connected to a sensing stage (62, 66) to record the atrial and/or left-ventricular depolarizations, which are then sent to a evaluation unit 280 as a component of the control unit 54, to determine the A-LV time as well as the atrial intervals (PP) and the left-ventricular intervals (LV). The evaluation unit 280 also performs a test of the A-LV times and the comparison of the PP and LV intervals plus tolerance. The comparison parameters (expected A-LV time, tolerance of the interval comparison, counter-criteria, minimum allowed LV interval) can be influenced from outside the cardiac stimulator 10 by programming. If the corresponding criteria are met in evaluation unit 280, the evaluation unit 280 generates a signal, which is forwarded to the treatment control unit 240 to block the shock therapy. If the parameter "block shock therapy due to electrode error" is activated in this treatment control unit, the signal for blocking the shock therapy with respect to the shock trigger is relayed, thereby suppressing the delivery of the shock in the event of a right-ventricular electrode error. In this configuration, the evaluation unit 280 functions in combination with the atrial and left-ventricular sensing units 62 and/or 66 as additional detection units.

Figure 4:
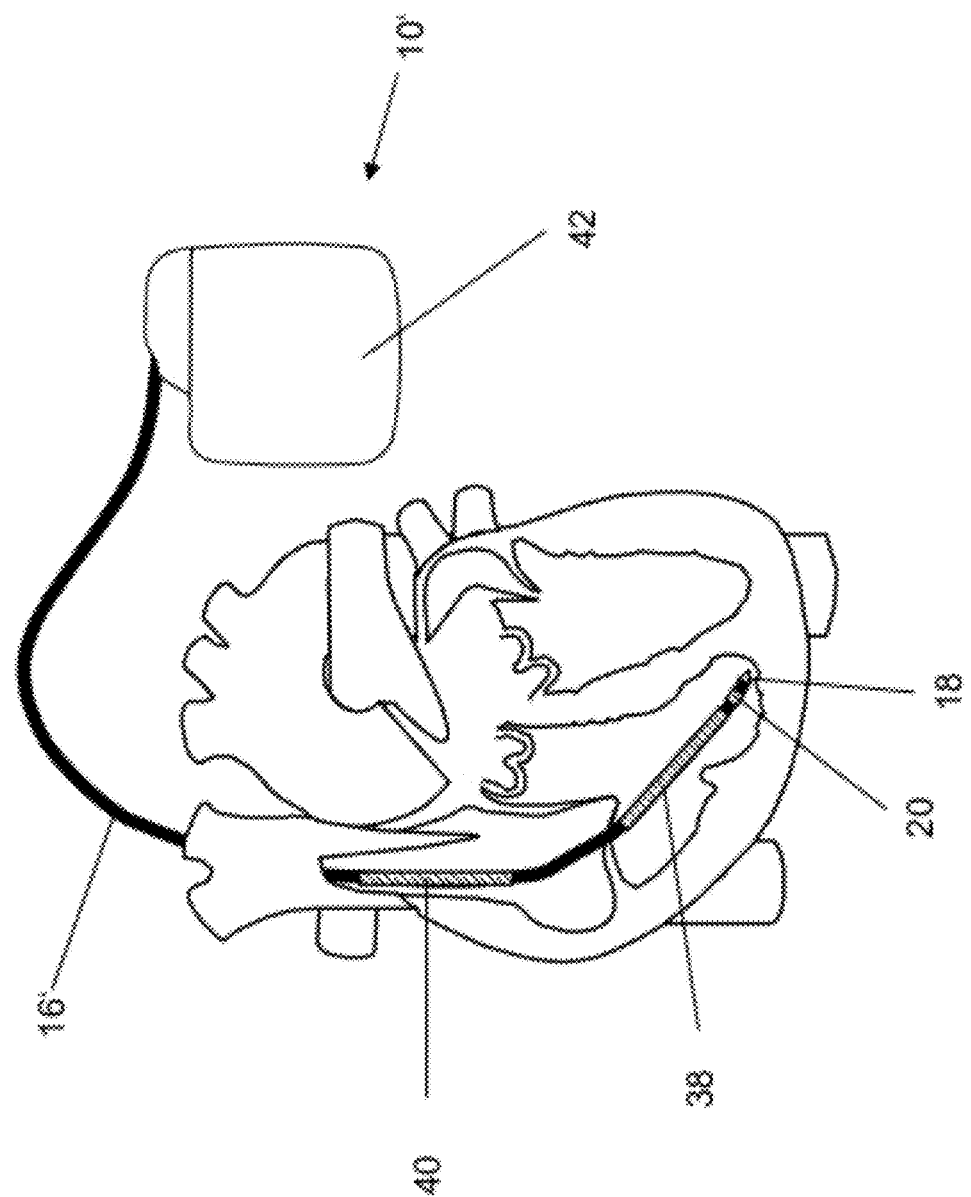
FIG. 4: shows a cardiac stimulator in the form of an implantable single-chamber ICD system.

FIG. 4 shows an alternative version of a cardiac stimulator 10' in the form of a single-chamber ICD. The cardiac stimulator 10' is connected to a right-ventricular electrode line 16', which also has two shock electrodes, namely a distal shock electrode 38 and a proximal shock electrode 40 in addition to the electrodes 18 and 20 for stimulation and sensing.

Figure 5:
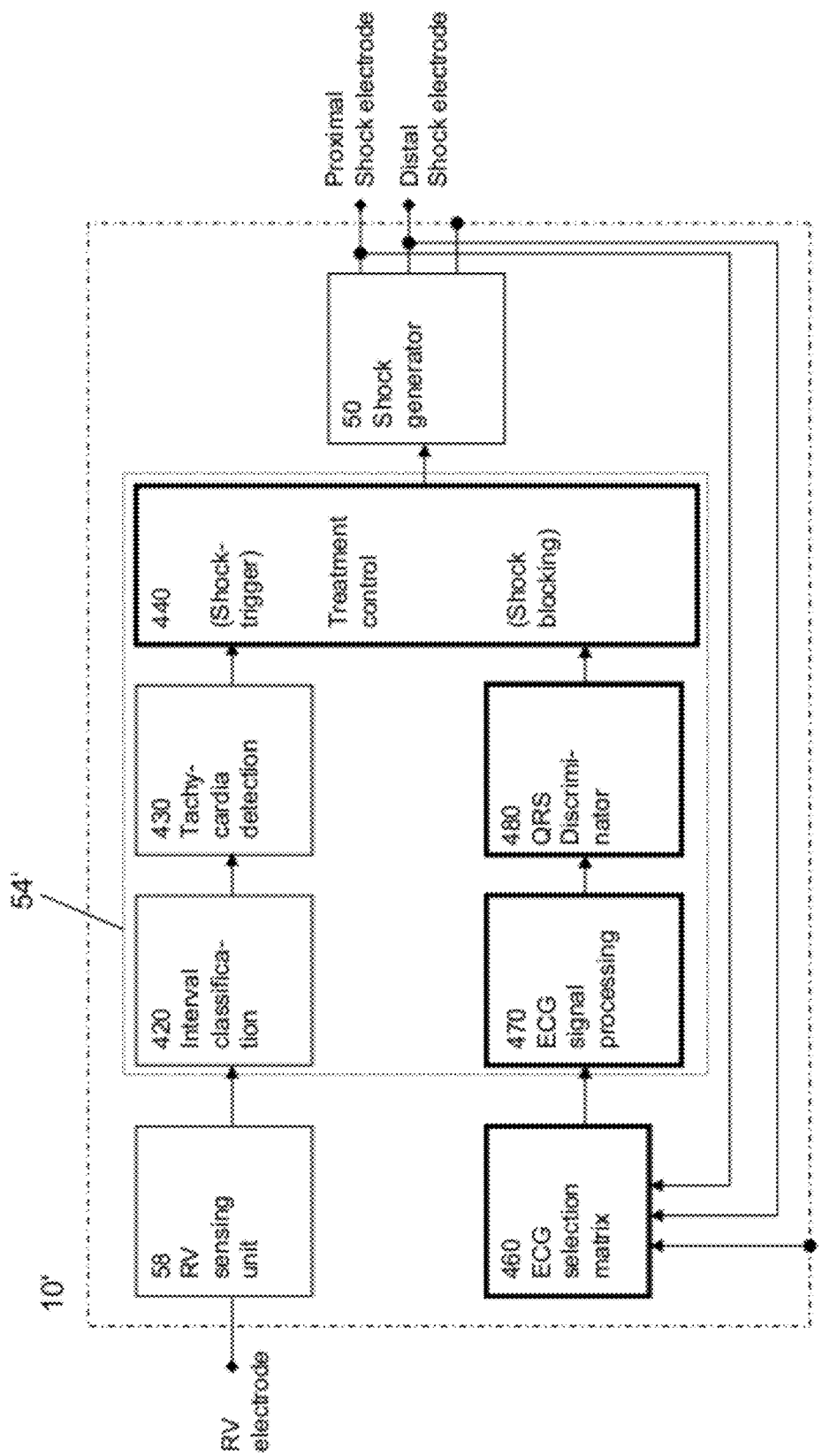
FIG. 5: shows a block diagram of a few relevant components of a single-chamber ICD system.

A simplified block diagram for the inventive implementation in a single chamber ICD system 10' is illustrated FIG. 5. The cardiac stimulator 10' has terminals for a right-ventricular electrode line 16' with stimulation and detection electrodes 18 and 20, and also has terminals for two defibrillation shock electrodes 38 and 40, both of which are situated on the right-ventricular electrode line 16'. The at least partially electrically conductive housing 42 at the ICD 10' constitutes another shock electrode for the delivery of a shock. The shock path used for defibrillation is adjustable via a selection matrix, e.g., selection matrix 460.

The right-ventricular electrode line 16' is connected to the (only) right-ventricular sensing unit 58'. This sensing unit 58' amplifies, digitizes and filters the IEGM derived by means of the electrode line 16' and extracts from it the points in time of the right-ventricular depolarization (sense). These sense events are then evaluated by an interval classifier 420 as a component of the control unit 54' according to the interval length, and are then sent to a detection counter 430 as an additional component of the control unit 54' for VF detection (primary ventricular fibrillation detection). This VF detection counter is preferably an X-of-Y counter, i.e., the VF zone limit must be exceeded for the VF detection criterion, i.e., X-of-Y intervals that have elapsed, to be met. If this VF criterion is met, then a trigger signal is sent to the treatment control unit 440 as a component of the control unit 54' for initiating shock therapy with the programmed parameters. This treatment control unit 440 then prompts the charging of the high voltage capacitors and the subsequent delivery of a shock by the shock generator 50.

The control unit 54' has an additional detection unit which includes an ECG selection matrix 460 and an ECG signal processing unit 470, and serves to record a far-field electrocardiogram. This is connected to an evaluation unit 480, which is designed to ascertain whether a far-field electrocardiogram recorded by means of the additional detection units 460 and 470 contains QRS complexes whose morphology is inconsistent with ventricular fibrillation.

The terminals for the shock electrodes 38 and 40 and the housing 42 of the ICD 10' are electrically connected to the ECG selection matrix 460. One of the following electrode configurations for the leads for a far-field electrocardiogram can be adjusted with this selection matrix 460 by programming:

distal shock electrode to housing (38-42);
proximal shock electrode to housing (40-42);
distal shock electrode to proximal shock electrode (38-40).

The potential differences applied to the selected electrodes are then amplified, digitized and filtered in the ECG signal processing unit 470, thus producing a far-field electrocardiogram. This preprocessed signal is then sent to a QRS discriminator 480 to detect the presence of QRS complexes in the signal. The QRS discriminator is preferably designed as a digital signal processor (DSP) to be able to implement universal algorithms for signal processing. The QRS discriminator checks on whether a QRS complex is present in the far-field IEGM in the last 2 . . . n seconds. If this criterion is met in the QRS discriminator, which serves as the evaluation unit 480, then a signal for blocking the shock therapy is sent to the treatment control unit 440. If the parameter "blocking shock therapy due to a electrode error" is activated in this treatment control unit, then the signal for blocking the shock therapy is sent through to the shock trigger, thereby suppressing the delivery of the shock in the event of a right-ventricular electrode error.

Figure 6:
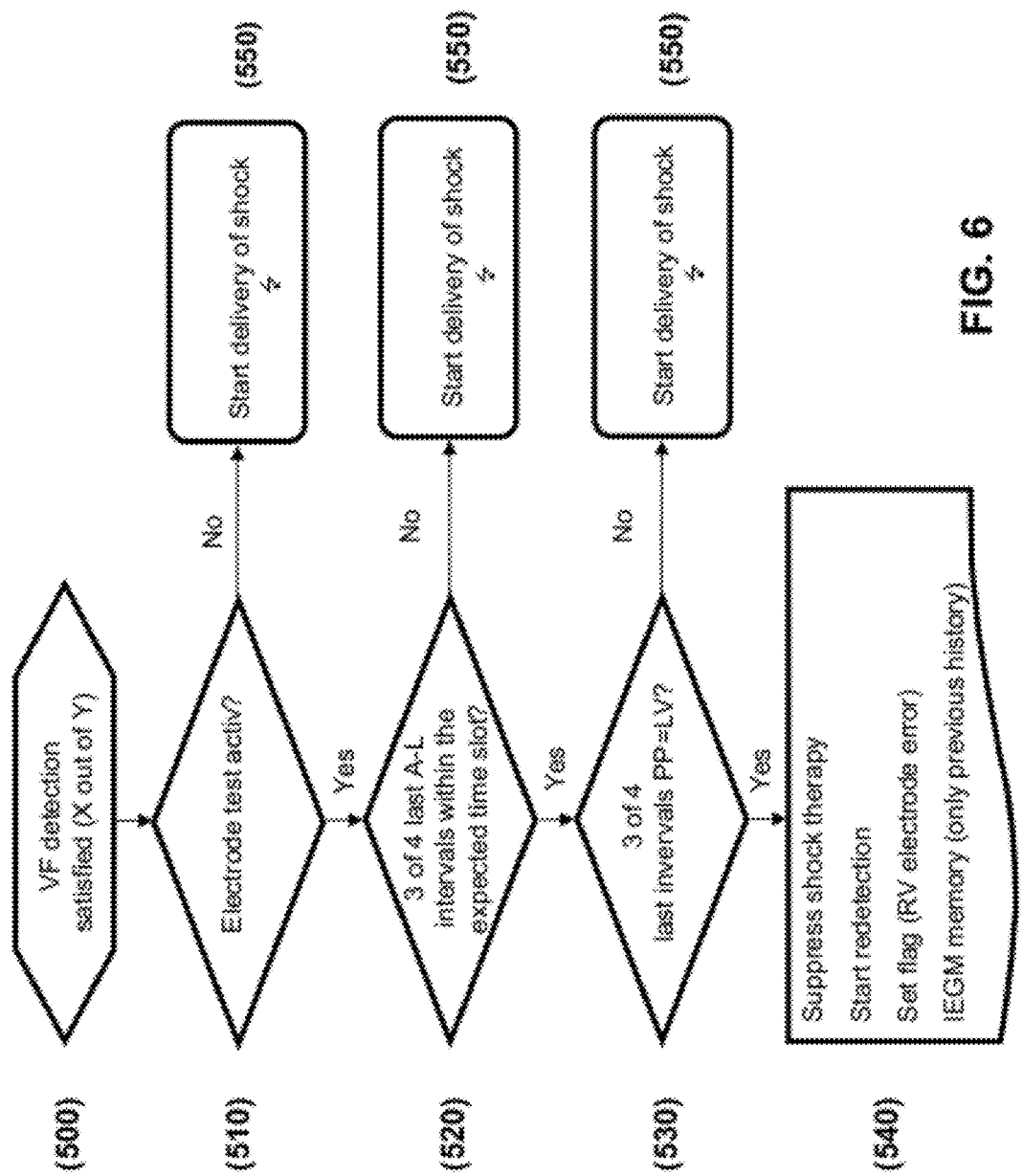
FIG. 6: shows a flow chart for electrode error detection in a triple-chamber ICD.

FIG. 6 shows the flow chart, which describes the control unit 54 with regard to its functioning in electrode error detection in the triple-chamber ICD 10 for FIGS. 1 to 3. After the VF detection criterion 500 has been met, based on right-ventricular sensing, a check 510 is performed on whether the function is activated for electrode testing. If this function is inactive, then the defibrillation shock is delivered in the normal way 550. If the function has been activated, the implant checks on whether an LV sense has occurred at least three times within the programmed expected interval after an atrial event in the last four A-LV event sequences. The three-of-four criterion makes the algorithm stable with respect to extrasystoles. If this condition is not met, the shock is usually delivered 550; otherwise, another test is performed to ascertain whether the past atrial intervals (PP) correspond to the LV interval 530 and whether the LV intervals are not faster than the programmed VF cycle length. This test is also linked to a three-of-four criterion and also allows a programmable tolerance (e.g., ±24 ms). If the intervals are not identical, the shock is usually delivered 550. If the intervals match, the shock therapy is suppressed and instead a redetection is initiated, the flag for displaying a right-ventricular electrode error is set and the so-called previous history of the VF detection is stored in the IEGM memory (e.g., the last 10 seconds before VF detection). Furthermore, this information can be transmitted automatically to a remote monitoring system.

Figure 7:
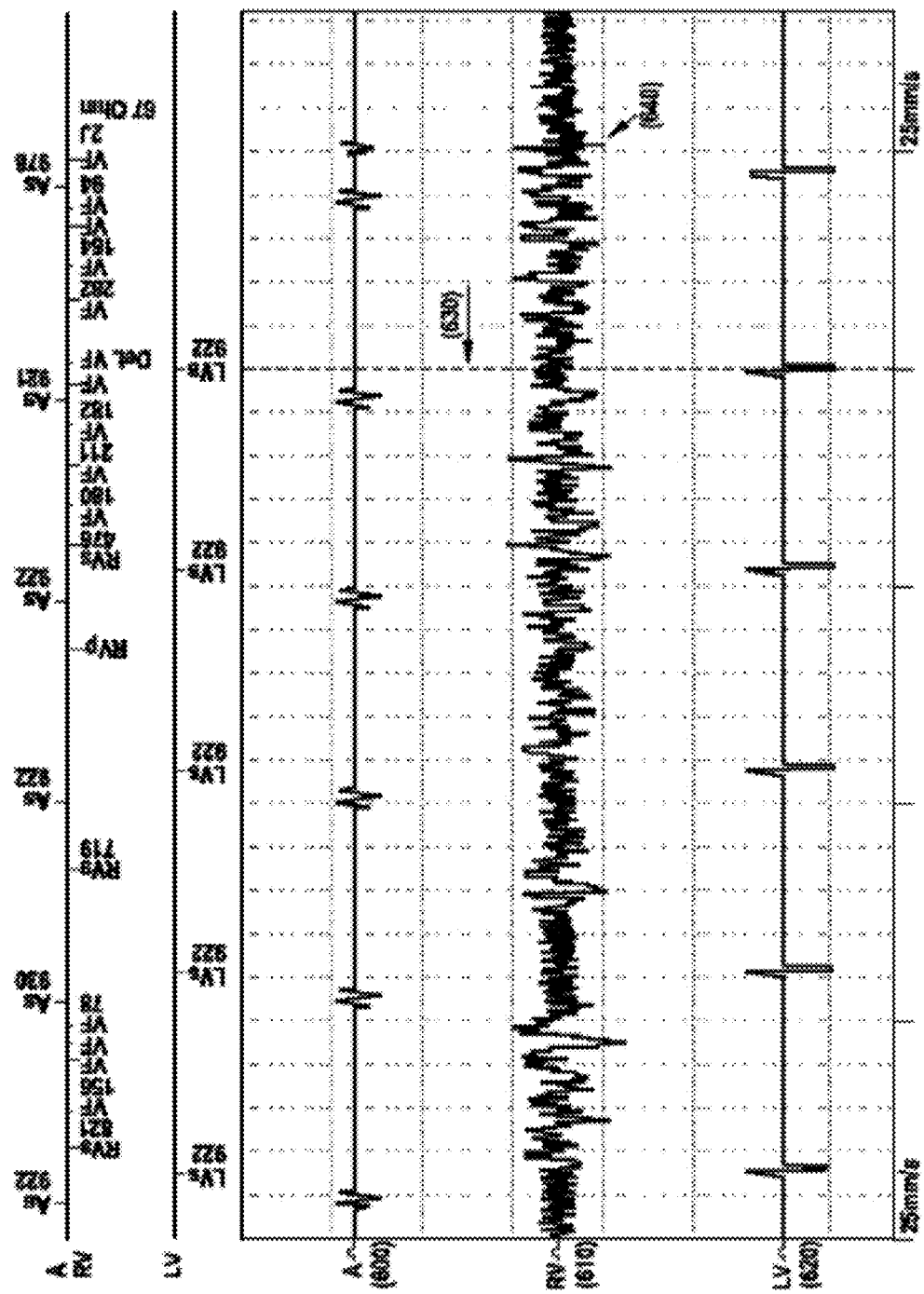
FIG. 7: shows an example of an inadequate shock due to an electrode defect.
Figure 8:
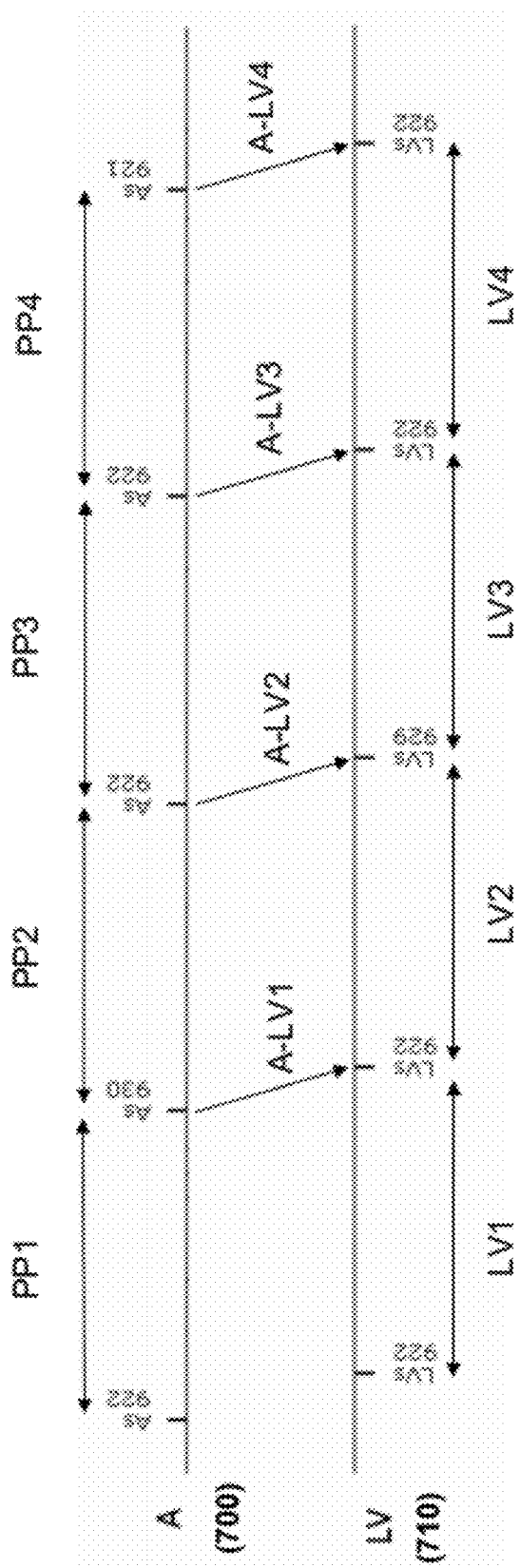
FIG. 8: shows atrial and left-ventricular markers from FIG. 7 in combination with the criteria to be checked for the electrode error detection.

FIGS. 7 and 8 illustrate the efficacy of this operation for electrode error detection. FIG. 7 shows a typical example of inadequate shock delivery due to a defective RV electrode 610. The atrial IEGM 600, the right-ventricular IEGM 610 (which includes interference), and the left-ventricular IEGM 620 are visible in the IEGM channels. Due to the interference in the RV channel 610, the criterion 630 for VF detection (8 out of 12 here) is met and then a shock 640 is delivered to the patient.

FIG. 8 shows the atrial markers 700 and the left-ventricular markers 710 from FIG. 7. In addition, the criteria for electrode error detection, which are to be tested in the method described here, are also shown. The sequence control first tests the A-LV intervals for the past four A-LV sequences (A-LV1 . . . 4). In this example, they are within the defined expected time slot. Likewise, the PP and LV intervals correspond (allowed tolerance±24 ms: PP1=LV1; PP2=LV2; PP3=LV3; PP4=LV4). In this case, the sequence control would declare the RV electrode to be defective and would suppress the delivery of the shock.

The invention is not intended to be limited to the preferred versions of the invention described above, but rather is intended to be limited only by the claims set out below. Thus, the invention encompasses all different versions that fall literally or equivalently within the scope of these claims.

What is claimed is:

1. An implantable cardiac stimulator (10) including:
   a. a defibrillation shock generator (50) in communication with a ventricular defibrillation electrode (38, 40),
   b. a right ventricular sensing unit (58) configured to receive electric signals of a right ventricle from a right ventricular sensing electrode (18, 20),
   c. at least one of:
      (1) an atrial electrode line (14) extending to an atrial sensing electrode (22, 24), the atrial electrode line (14) being configured to convey signals indicative of atrial events, and
      (2) a left-ventricular electrode line (30) extending to a left-ventricular sensing electrode (32, 34), the left-ventricular electrode line (30) being configured to convey signals indicative of left-ventricular events,
   d. a control unit (54, 54') in communication with the right ventricular sensing unit (58) and the defibrillation shock generator (50), the control unit (54, 54') being configured to:
      (1) monitor the right ventricular rhythm from the right-ventricular sensing electrode (18, 20),
      (2) detect ventricular fibrillation therein, and
      (3) trigger the defibrillation shock generator (50) to deliver a defibrillation shock via the ventricular defibrillation electrode (38, 40) if ventricular defibrillation is detected,
   e. a evaluation unit (280, 460, 470) in communication with the control unit (54, 54'), wherein the evaluation unit (280, 460, 470) is:
      (1) configured to derive the right ventricular rhythm independently of the right ventricular rhythm monitored from the right-ventricular sensing electrode (18, 20) on the basis of at least one of
         (a) left-ventricular events, and
         (b) atrial events, and
      (2) configured to suppress the delivery of a defibrillation shock upon detection of a normal right ventricular rhythm.

2. The implantable cardiac stimulator (10) of claim 1 wherein the implantable cardiac stimulator (10) includes a memory (80) storing information regarding the suppression of the delivery of the defibrillation shock.

3. The implantable cardiac stimulator (10) of claim 1 wherein the evaluation unit (480) is configured to detect a right ventricular rhythm as normal when QRS complexes are identified within a far-field electrocardiogram.

4. The implantable cardiac stimulator (10) of claim 3 wherein QRS complexes are identified in the far-field electrocardiogram via sample comparison.

5. The implantable cardiac stimulator (10) of claim 3 wherein QRS complexes are identified in the far-field electrocardiogram via identification of signal peaks characteristic of ventricular events.

6. The implantable cardiac stimulator (10) of claim 3 wherein the evaluation unit (280, 460, 470) is further configured to derive the right ventricular rhythm from a far field electrocardiogram obtained from electrodes other than the right ventricular sensing electrode (18, 20).

7. The implantable cardiac stimulator (10) of claim 1 wherein
   the evaluation unit (280) is configured to detect a right ventricular rhythm as normal when:
      (1) a single left-ventricular event is detected within a predefined time interval after an atrial event, and
      (2) the interval between successive left-ventricular events is at least substantially equal to the interval of the preceding atrial events.

8. The implantable cardiac stimulator (10) of claim 7 wherein the predefined time interval is manually adjustable.

9. The implantable cardiac stimulator (10) of claim 1 wherein:
   a. the cardiac stimulator (10) includes an at least partially electrically conductive housing (42), and
   b. the evaluation unit (460, 470) is configured to derive a far-field electrocardiogram from signals obtained from a pair of spaced electrodes, wherein one of the electrodes is defined by the housing (42).

10. The implantable cardiac stimulator (10) of claim 9 wherein the other of the electrodes is defined by the ventricular defibrillation electrode (38, 40).

11. The implantable cardiac stimulator (10) of claim 1 wherein:
   a. the cardiac stimulator (10) includes an at least partially electrically conductive housing (42),
   b. the evaluation unit (460, 470) is configured to derive a far-field electrocardiogram from signals obtained from:
      (1) the housing (42), and
      (2) the ventricular defibrillation electrode (38, 40), and
   c. the implantable cardiac stimulator (10) includes an electrocardiogram evaluation unit (480) is configured to identify ventricular depolarizations within the far-field electrocardiogram, and
   d. the evaluation unit (280, 460, 470) is configured to derive the right ventricular rhythm from the ventricular depolarizations.

12. The implantable cardiac stimulator (10) of claim 11 wherein:
   a. the ventricular defibrillation electrode (38, 40) includes:
      (1) a proximal electrode (40) and
      (2) a distal electrode (38) separate and spaced from the proximal electrode, and
   b. one of the proximal electrode (40) and the distal electrode (38) is used to obtain the far field electrocardiogram.

13. The implantable cardiac stimulator (10) of claim 1 wherein:
   a. the cardiac stimulator (10) includes an at least partially electrically conductive housing (42),
   b. the ventricular defibrillation electrode (38, 40) includes a proximal electrode (40) and a distal electrode (38), and
   c. the evaluation unit (460, 470) is configured to derive a far-field electrocardiogram from signals obtained from two of:
      (1) the housing (42),
      (2) the proximal electrode (40), and
      (3) the distal electrode (38).

14. The implantable cardiac stimulator (10) of claim 13 wherein:
   a. the implantable cardiac stimulator (10) includes an electrocardiogram evaluation unit (480) configured to identify ventricular depolarizations within the far-field electrocardiogram, and b. the evaluation unit (280, 460, 470) is configured to derive the right ventricular rhythm from the ventricular depolarizations.

15. The implantable cardiac stimulator (10) of claim 13 wherein:
- a. the evaluation unit (460, 470) is configured to derive a far-field electrocardiogram from signals obtained from the proximal electrode (40) and the distal electrode (38),
- b. the implantable cardiac stimulator (10) includes an electrocardiogram evaluation unit (480) configured to identify ventricular depolarizations within the far-field electrocardiogram, and
- c. the evaluation unit (280, 460, 470) is configured to derive the right ventricular rhythm from the ventricular depolarizations.

16. The implantable cardiac stimulator (10) of claim 1:
- a. including:
  - (1) an at least partially electrically conductive housing (42),
  - (2) an atrial electrode line (14) extending to an atrial sensing electrode (22, 24),
- b. wherein the evaluation unit (460, 470) is configured to derive:
  - (1) a far-field electrocardiogram from signals obtained from the housing (42) and the atrial sensing electrode (22, 24), and
  - (2) the right ventricular rhythm from ventricular depolarizations identified within the far-field electrocardiogram.

17. The implantable cardiac stimulator (10) of claim 1 wherein the right-ventricular sensing electrode (18, 20) has a smaller area than the defibrillation electrode (38, 40).

18. An implantable cardiac stimulator (10) including:
- a. an at least partially electrically conductive housing (42),
- b. a defibrillation shock generator (50) in communication with a ventricular defibrillation electrode (38, 40),
- c. a right-ventricular sensing unit (58) configured to receive electric signals of a ventricle from a right-ventricular sensing electrode (18, 20),
- d. at least one of:
  - (1) an atrial electrode line (14) extending to an atrial sensing electrode (22, 24), and
  - (2) a left-ventricular electrode line (30) extending to a left-ventricular sensing electrode (32, 34),
- e. a control unit (54, 54') in communication with the right-ventricular sensing unit (58) and the defibrillation shock generator (50), the control unit (54, 54') being configured to:
  - (1) monitor the right ventricular rhythm from the right-ventricular sensing electrode (18, 20),
  - (2) detect ventricular fibrillation therein, and
  - (3) trigger the defibrillation shock generator (50) to deliver a defibrillation shock via the ventricular defibrillation electrode (38, 40) if ventricular defibrillation is detected,
- f. a evaluation unit (280, 460, 470) in communication with the control unit (54, 54'), wherein the evaluation unit (280, 460, 470) is configured to suppress delivery of the defibrillation shock based on near-field signals obtained solely from one or more of:
  - (1) the atrial sensing electrode (22, 24), and
  - (2) the left-ventricular sensing electrode (32, 34),
  in the event such signals are indicative of a normal right ventricular rhythm.

19. The evaluation unit of claim 18 wherein:
- a. the evaluation unit (280, 460, 470) is configured to obtain signals from:
  - (1) the atrial sensing electrode (22, 24), and
  - (2) the left ventricular sensing electrode (32, 34),
- b. the delivery of the defibrillation shock is suppressed when:
  - (1) a single left ventricular event is detected within a predefined time interval after an atrial event, and
  - (2) the interval between successive left ventricular events at least substantially matches the interval of the preceding atrial events.

20. The implantable cardiac stimulator (10) of claim 19 wherein the predefined time interval is manually adjustable.

* * * * *